United States Patent [19]

Fielder et al.

[11] Patent Number: 5,460,969
[45] Date of Patent: Oct. 24, 1995

[54] METHOD FOR DIFFERENTIATING THE SOURCE OF OCCULT GASTROINTESTINAL BLEEDING

[76] Inventors: Paul N. Fielder, 200 Hemlock Rd., New Haven, Conn. 06515; Robert A. Levine, 31 Pilgrim La., Guilford, Conn. 06437; Stephen C. Wardlaw, 128 Sunset Hill Dr., Branford, Conn. 06405

[21] Appl. No.: 31,544

[22] Filed: Mar. 15, 1993

[51] Int. Cl.$^6$ .................................................. G01N 33/72
[52] U.S. Cl. ............................ 436/66; 436/175; 128/638; 128/759; 435/28
[58] Field of Search ........................... 436/66, 170, 175, 436/178, 177; 128/638, 759; 422/56, 58, 61; 435/28, 805

[56] References Cited

U.S. PATENT DOCUMENTS

| | | | |
|---|---|---|---|
| 3,718,431 | 2/1973 | Wild | 436/66 |
| 3,996,006 | 12/1976 | Pagano | 422/50 |
| 4,175,923 | 11/1979 | Friend | 436/66 |
| 4,259,964 | 4/1981 | Levine | 128/638 |
| 4,273,741 | 6/1981 | Levine | 422/56 |
| 4,367,750 | 1/1983 | Levine | 128/638 |
| 4,420,353 | 12/1983 | Levine | 156/227 |
| 4,559,949 | 12/1985 | Levine | 128/638 |
| 4,615,982 | 10/1986 | Lawrence | 436/66 |
| 4,645,743 | 2/1987 | Baker et al. | 436/66 |
| 4,789,629 | 12/1988 | Baker et al. | 435/7 |
| 4,804,518 | 2/1989 | Levine et al. | 422/56 |
| 4,808,379 | 2/1989 | Wardlaw et al. | 422/56 |
| 4,849,173 | 7/1989 | Chang | 422/56 |
| 4,956,300 | 9/1990 | Wells | 436/66 |
| 5,064,766 | 11/1991 | Wardlaw et al. | 436/66 |
| 5,094,956 | 3/1992 | Grow et al. | 436/66 |
| 5,128,452 | 7/1992 | Hai et al. | 530/385 |

OTHER PUBLICATIONS

Lemberg et al., Hematin Compounds and Blue Pigments 1949 pp. 159–175, 223–225.
"Cytologic Detection of Colorectal Cancer After . . . ", by Gordon et al., pp. 106–110, Jul. 1, 1991.
"A Method of Obatining, Processing, and Analyzing . . . ", by Gaspari et al., *Journal of Immun. Methods*, pp. 85–91, 1988.
"Gut Lavage Fluid Proteins as Markers . . . ", by S. O'Mahony et al., pp. 940–944, 1991.
"Haemoglobin in Gut Lavage Fluid as a Measure of Gastrointestinal Blood Loss," *The Lancet*, vol. 340, pp. 1381–1382, Dec. 5, 1992.

*Primary Examiner*—James C. Housel
*Assistant Examiner*—Rachel Heather Freed
*Attorney, Agent, or Firm*—Price, Heneveld, Cooper, DeWitt & Litton

[57] ABSTRACT

The presence of fecal occult blood in a stool sample is detected by mixing a liquid stool sample with an acidic liquid, such as a phosphate/citrate buffer, to precipitate hematin from the solution. The precipitated hematin is separated and the presence or absence of hemoglobin is determined by exposing the solution to a peroxidase diagnostic assay. A positive response indicates the presence of blood originating in the lower gastrointestinal tract, a leading indicator of lower GI cancer.

27 Claims, No Drawings

METHOD FOR DIFFERENTIATING THE SOURCE OF OCCULT GASTROINTESTINAL BLEEDING

BACKGROUND OF THE INVENTION

The present invention relates to a method for differentiating the source of occult gastrointestinal bleeding.

The common screening test for occult gastrointestinal bleeding is to test for fecal occult blood (FOB). An FOB test involves placing a sample of stool onto a testing surface and adding one or more reagents which react with the blood in the sample to produce a recognizable color.

Two current varieties of such tests are the HEMOCCULT device and the HEMAWIPE device. The HEMOCCULT test device requires that one use a small paddle to fish a feces sample out of the toilet and apply the sample to a piece of test paper mounted on a card. U.S. Pat. No. 3,996,006 to Pagano is exemplary of a HEMOCCULT test device.

The HEMAWIPE device utilizes a test pad adhered to a pliant impermeable base sheet and covered with a pliant volume control sheet having openings therein in alignment with the test pad. The patient can wipe with the HEMAWIPE device, remove the volume control cover sheet, fold the pliant base sheet over on itself to seal the test pad and sample and submit it for testing. A number of prior patents relate to the HEMAWIPE device including U.S. Pat. No. 4,808,379 entitled DEVICE FOR OBTAINING STOOL SAMPLES, issued Feb. 18, 1989; U.S. Pat. No. 4,804,518, entitled DEVICE FOR OCCULT BLOOD TESTING, issued Feb. 14., 1989; U.S. Pat. No. 4,559,949, entitled STOOL SAMPLING DEVICE, issued Dec. 24, 1985; U.S. Pat. No. 4,420,353, entitled METHOD OF MAKING A STOOL SAMPLING DEVICE, filed Dec. 13, 983; U.S. Pat. No. 4,367,750, entitled DEVICE FOR OBTAINING STOOL SAMPLES, issued Jan. 11, 1983; U.S. Pat. No. 4,273,741, entitled DEVICE FOR OBTAINING STOOL SAMPLES, issued Jun. 16, 1981; and U.S. Pat. No. 4,259,964 entitled DEVICE FOR OBTAINING STOOL SAMPLES, issued Apr. 7, 1981.

Virtually all FOB tests used today have the problem of nonspecificity. Their chemical reactions detect the peroxidase property of hemoglobin by causing the catalysis of peroxide into oxygen and water, and the subsequent oxidation of a colorless die into a colored form. Gum guaiac is the most commonly used color reagent, although a large number of other reagents have been used in the past.

The nonspecificity is due to two reasons. First, there are other peroxidase containing materials which the patient may eat, which, when excreted, will also cause a positive reaction. Second, blood from gastritis or dental bleeding can cause a positive reaction as well. While the hydrochloric acid present in the normal stomach converts the hemoglobin in the blood to hematin, hematin also has peroxidase activity material which can cause false-positives. Ideally, an FOB test would not only reliably detect blood but also give some indication as to the origin of the blood.

Since the FOB tests are more frequently used to screen patients for a hidden colonic malignancy, the consequences of missing any bleeding can be severe. Conversely, if there are a large number of false positive tests, the expense and possible complications of the additional follow-up tests involved are also considerable.

The ability to discriminate between the source of bleeding can play a pivotal role in the work-up and management of the patient with occult gastrointestinal bleeding. Detection of hematin in the stool will signify upper GI blood loss or the ingestion of peroxidases including blood in the diet. The clinician will be advised to repeat the test following dietary manipulation or proceed directly to upper endoscopy and/or radiographic study of the esophagus and stomach. Detection of hemoglobin in the stool, however, will focus clinical attention toward diseases of the distal GI tract including colonic carcinoma or polyposis, hemorrhoids or rectal fissures. The differential diagnosis will not be obscured by dietary sources or gastric stress ulcers, common causes of "false positive" results with HEMOCCULT and HEMAWIPE test systems.

There have been many attempts to make the FOB test more specific while preventing the undesired false positive results. Specific immunologic tests have been employed which are reactive only to human blood. The problem with these have been that they are much more complicated and expensive than the usual screening test, and the blood may be altered by partial digestion so that it is not detected by immunologic means. A recent technique called HEMAQUANT involves the extraction of a stool sample to obtain porphyrins, the breakdown products of blood. The advantage of this technique is that it is quantitative and relatively specific, but it too is expensive and much more cumbersome than the usual screening tests.

Therefore, there is a need to provide a FOB test which allows for the differential diagnosis of upper GI bleeding from lower GI bleeding which is inexpensive, easy to use, and provides adequate sensitivity, while preventing undesired false positive results.

SUMMARY OF THE INVENTION

In the present invention, a liquid stool sample is prepared in which fecal material is dispersed in solution to dissolve any hematin and hemoglobin present in the stool sample. Hematin is preferentially precipitated and separated from the solution. The remaining solution is subjected to a diagnostic assay for peroxidase activity. Since hemoglobin which has passed through the stomach and upper gastrointestinal tract will have been substantially converted to hematin by stomach acid, the presence of peroxidase activity in the separated solution is an indication of the presence of hemoglobin only, which has originated in the lower gastrointestinal tract.

Since upper GI bleeding is more typically an indication of ulcers rather than cancer, a positive result in accordance with the test of the present invention is a superior indication of the possible presence of cancer. In addition, the elimination of hematin from the test sample eliminates dietary blood as a source of false positive. The sensitivity of the diagnostic assay can be increased greatly without risking an undue increase in the number of false positives.

DETAILED DESCRIPTION OF THE INVENTION

In the preferred embodiment, a liquid stool sample is prepared in which fecal material is dispersed in solution. This dispersion tends to dissolve any hematin and hemoglobin which may be present in the fecal material. Hematin is preferentially precipitated by acidifying the liquid stool sample. Separation is effected by filtration and the remaining solution is subjected to a peroxidase sensitive diagnostic assay.

In the preferred embodiment, a laxative purge is ingested and the first watery stool is collected. Solid stool present in the rectum and sigmoid colon at the time the purge is initiated is evacuated soon after the laxative is administered. This material is discarded unless a baseline value is sought. The first watery stool passed usually contains at least some fecal material that has been rapidly transported through the colon. While this sample may be suitable for some assays, in most situations stools collected later during the purge will be of greater diagnostic utility.

Additionally, two alternative embodiments are disclosed. In the first, the laxative purge is administered immediately after a bowel movement and the first and subsequent watery post-purge bowel movements are collected in separate containers. In the second embodiment, the purge is administered to the patient, any solid stool and the first watery post-purge bowel movement is discarded and the second and subsequent watery post-purge bowel movements are collected in separate containers. Each of these embodiments provides the opportunity to obtain stool samples having a higher yield of FOB because the collected stool has a shorter residency time in the colon.

The preferred method for preparing the liquid stools, and thereby dispersing fecal material in solution, is to administer a laxative purge to the patient. Ideally, the laxative purges are administered to the patient orally. While in the broader aspects of the invention, a conventionally obtained stool sample could be mechanically dispersed in solution, it is more preferred to prepare the liquid stool sample "in situ" by using the laxative purge. This minimizes residence time of the stool in bowel, and makes the end results of the assay more reliable.

Preferred stool samples are obtained by administering a purgative dose (1.5 ounces) of FLEET PHOSPHO soda, containing as active ingredients monobasic sodium phosphate and dibasic sodium phosphate. Another preferred purge is magnesium citrate. Preferred laxative purges not only reduce the residence time of a patient's stool in the large bowel, they also do not affect the FOB present in the stool in order to facilitate proper diagnostic testing. In addition, preferred laxative purges maintain the chemical and biologic integrity of stool samples to allow the stool to be stored for a period of time after collection prior to testing. A particularly preferred laxative purge is a PHOSPHO soda purge available from FLEET Inc., Lynchburg, Va. Use of these laxatives also diminishes hemorrhoidal bleeding, a source of false positive results in occult colon cancer screening.

To obtain a proper liquid stool sample, the patient must ingest sufficient laxative purge. Generally, sufficient liquid stool is obtained by following the manufacturer's instructions. It is within the ability of one of ordinary skill in the art to determine the proper dosage of the purge if variation is required.

If after the ingestion of the purge, the first post-purge bowel movement is solid, the first post-purge bowel movement is discarded and the first watery stool is collected. If the second bowel movement remains solid, a second laxative purge can be administered to the patient and the first watery bowel movement excreted by the patient is collected. Following collection, the fecal sample is then subjected to diagnostic testing.

If testing is not going to be immediate, liquid stool samples obtained by laxative purge may be stable for about one to two days at room temperature and about five days if refrigerated following collection. Addition of a preservative such as ethylenediamine-tetraacetic acid (EDTA) can enhance the stability of the sample even more.

Hematin tends to precipitate preferentially as the liquid stool sample is rendered more acidic. In the preferred embodiment, the pH of the solution is lowered to about pH 3.5 to about 5.0 through the use of an acidic pH buffer, such as MCILVAINE'S buffer.

One volume of liquid stool is mixed with from about five to about ten volumes, and preferably five volumes, of MCILVAINE'S buffer, a phosphate/citrate buffer, to form an acidified liquid fecal sample solution. Other acidic buffers can be used.

The acidified liquid fecal sample solution is then subjected to filtration through Whatman #2 filter paper. Other size-dependent, or density dependent, separation procedures can be used to separate any precipitate from the solution such as centrifugation.

The presence or absence of hemoglobin is then determined by exposing the filtrate, or supernatant following centrifugation, to a hemoglobin diagnostic assay designed to detect peroxidase activity. Among the preferred diagnostic assays is the AMES urine dipstick having the "blood" test pad.

The sensitivity of the test can be varied by varying three factors:

1) the extent to which the liquid stool sample is diluted with buffer;

2) the number of filters used, i.e., one sheet of filter paper versus two or three; and 3) the intensity of the peroxidase activity indication, i.e., hemolyzed trace, small, medium or large which is accepted as a positive cutoff value.

These limits of sensitivity are explored, along with the fundamental efficacy of the present invention, in the experimental and clinical results discussed below.

EXPERIMENTAL RESULTS

Liquid stool samples obtained by purge from several different patients were spiked with either whole blood or hematin prior to mixing with the acidic buffer. The results obtained are illustrated in the following tables in which "Hgb" "ul" and "ug" symbolize hemoglobin, microliters and micrograms, respectively. In addition, the level of peroxidase activity in the filtrate is indicated in the tables as follows: L=large, M=medium, S=small, HT=hemolyzed trace, and N=negative. Further, since the ratio of the molecular weight of hemoglobin to hematin is 100:1, 100 micrograms of hemoglobin is the molar equivalent of 1 microgram of hematin. The effect of using multiple layers of a filter paper was also evaluated.

| SELECTIVE PRECIPITATION OF STOOL PEROXIDASES | | | | |
|---|---|---|---|---|
| Addition to | NUMBER OF FILTERS | | | |
| 1 ml sa | 0 | 1 | 2 | 3 |
| | PATIENT: A | | | |
| nothing | L | HT | HT | N |
| 1 ul blood (100 ug Hgb) | L | M | HT | N |
| 0.1 ul blood (10 ug Hgb) | L | S | HT | N |
| 0.01 ul blood (1 ug Hgb) | L | HT | HT | N |
| 10 ug hematin | L | HT | HT | N |

-continued

SELECTIVE PRECIPITATION
OF STOOL PEROXIDASES

| Addition to 1 ml sa | NUMBER OF FILTERS | | | |
|---|---|---|---|---|
| | 0 | 1 | 2 | 3 |
| PATIENT: B | | | | |
| nothing | L | HT | N | N |
| 1 ul blood (100 ug Hgb) | L | N | S | N |
| 0.1 ul blood (10 ug Hgb) | L | S | N | N |
| 0.01 ul blood (1 ug Hgb) | L | HT | N | N |
| 10 ug hematin | L | HT | N | N |
| PATIENT: C | | | | |
| nothing | L | HT | HT | N |
| 1 ul blood (100 ug Hgb) | L | M | HT | N |
| 0.1 ul blood (10 ug Hgb) | L | S | HT | N |
| 0.01 ul blood (1 ug Hgb) | L | HT | HT | N |
| 10 ug hematin | L | HT | HT | N |

The trial for each patient where no hemoglobin or hematin was added to the stool samples (entitled "nothing") indicates the base line level of peroxidase activity in each stool sample. The data indicate that the unfiltered stool samples always demonstrate a high level of peroxidase activity regardless of spiking with hemoglobin or hematin. When passed through a single layer of filter paper, however, the data indicate that the higher levels of spiked hemoglobin are able to penetrate the filter paper, while hematin and lower levels of spiked hemoglobin do not.

Specifically, in each of the trials using one layer of filter paper, separate additions of 10 and 100 micrograms of hemoglobin to the liquid stool samples increased the level of peroxidase activity detected in the filtrate. This increase in peroxidase activity indicated that these levels of hemoglobin were able to penetrate the single layer of filter paper. Without wishing to be bound by any particular theory, it is postulated that addition of 1 microgram of hemoglobin to the stool samples had no measurable effect in the peroxidase activity of the sample because the hemoglobin was retained by the filter paper.

The data illustrate that increasing the number of layers of filter paper through which the stool sample flows had a measurable effect on peroxidase activity. Again, without wishing to be bound by any particular theory, it is postulated that the increase in the number of layers of filter paper resulted in an increase in the amount of hemoglobin retained by the filter paper which reduced the peroxidase activity.

The data regarding the addition of 10 micrograms of hematin to the liquid stool samples indicate that the hematin precipitated and did not penetrate the filter paper. In each trial, regardless of the layers of filter paper, the peroxidase activity in the filtrate did not increase when hematin was added to the stool samples. Therefore, the data support a conclusion that hematin may be selectively removed from liquid stool.

The use of the very small quantity of hemoglobin, one microgram, and the use of multiple layers of filter paper are helpful in establishing the limits of sensitivity of the test. The fact that the test is sensitive to a level of at least as low as 10 micrograms of hemoglobin indicates that the test is highly sensitive and effective in detecting fecal occult blood originating in the lower gastrointestinal tract. The fact that it was not sensitive to one microgram is not of substantial concern as a practical matter. To the extent that filter paper is used as the medium for separating precipitated hematin, it is preferable that a single layer of filter paper be used rather than two or three layers.

CLINICAL STUDIES

To demonstrate the clinical utility of this assay in detecting malignant and pre-malignant lesions of the large bowel, a trial was conducted on patients scheduled for colonoscopy. The patients collected their second watery stool sample passed after taking a purgative the night before the colonoscopy. Samples were collected in a clean plastic container and were refrigerated overnight. Testing was performed on all samples within 24 hours of collection. The procedure used was as indicated above, with the exception that a 1:5 dilution of sample in buffer was also included, in addition to the 1:10 dilution used above. The same notations used above to indicate the level of peroxidase activity in the filtrate are used below.

All 76 of the patients had been recommended for endoscopy because their physicians had indicated that they were likely candidates for colon cancer. They had either tested positive for fecal occult blood in a conventional fecal occult blood test, or they had a strong family history of colon cancer, or they had shown indications of adenomatous polyps during previous endoscopies.

The sensitivity of the test was varied in three ways. First, a volume of liquid stool sample was diluted 1:5 and 1:10 to determine the impact of dilution on sensitivity. Secondly, one set of samples diluted 1:10 were filtered through only one filter and another set were filtered through two filters, to determine the impact of the number of filters on the test sensitivity. Thirdly, the results were compared by first assuming that either a small or moderate showing of peroxidase activity constituted a positive indication, as compared to using only a moderate showing as a positive indication.

PATIENT DATA SUMMARY

Total number of stool samples—76
Endoscopy/pathology findings
  Detected premalignant or malignant lesions:
  26 patients—small adenomatous polyp(s)<1.0 cm
  2 patients—adenomatous polyp>1.0 cm
  1 patient—villous adenoma (2 cm)
  1 patient—diffuse involvement of mucosa by leukemia (CLL)

Of the above conditions, the only one which all doctors would agree is a "must find" is the presence of the villous adenoma. Many physicians would consider it desirable to identify the larger polyps, i.e., greater than one centimeter. These would be of interest as an indication of possible future activity, even though the presence of the larger polyps is not a basis for pursuing surgery.

The presence of small polyps would not be considered relevant by most physicians. The involvement of mucosa by leukemia is a rare condition and is also not a basis for colon surgery. Hence, identifying this condition would also be considered unnecessary and, indeed, would constitute a "false positive" in the context of a fecal occult blood test.

RESULTS OF F.O.B. TESTING IN ACCORDANCE WITH THIS INVENTION:

| PEROXIDASE ACTIVITY | DILUTITION/FILTER NUMBER | | |
|---|---|---|---|
| | 1:5/1 FILTER | 1:10/1 FILTER | 1:10/2 FILTERS |
| S OR M | 32/76 | 16/76 | 1/76 |
| | 13/26 small polyps | | |
| | 2/2 polyps> 1.0 cm | 1/2 polyps> 1.0 cm | |
| | 1/1 villous adenoma | | |
| | 1/1 leukemia | 1/1 leukemia | |
| M | 8/76 | 2/76 | 0/76 |
| | 1/1 villous adenoma | | |

The above data reveal that 32 of the 76 samples, when filtered through 1 filter, had a small or medium level of peroxidase activity in their filtrate at a 1:5 dilution. If a small or medium level of activity is considered "positive," then 32 of the 76 patients tested "positive" for the presence of blood in their stool. The endoscopic examination data also reveal that 30 of the 76 patients had detectable lesions in the form of small polyps (<1.0 cm), adenomatous polyps (>1.0 cm), villous adenoma (2.0 cm) or diffuse involvement of mucosa by leukemia. Combination of the data reveals that 13/26 of the patients with small polyps tested positive for the presence of blood in their stool and 100% of the patients with clinically significant pathologic lesions tested positive for the presence of blood in their stool.

Under clinical definitions, polyps are not considered by most physicians to be worrisome lesions until their size is greater than 1 centimeter. Therefore, the fact that 50% of the patients with small polyps did not display peroxidase activity is not significant. While the positive peroxidase test activity displayed by some of the small polyps does constitute a false positive, the conclusion which can be drawn from the data is that 100% of the clinically significant pathologic lesions are identified when small or medium levels of peroxidase activity are detected in stool filtrates filtered through 1 filter at a 1:5 dilution. Of the 76 patients for whom endoscopy had been ordered, 44 could have gone home without this expensive procedure if the test of the present invention had been administered.

A review of the data relating to the use of a 1:10 dilution/1 filter allows a similar analysis. At 1:10/1 filter, 16/76 samples had a small or medium level of peroxidase activity in their filtrate. An advantage of this dilution level is that no peroxidase activity was found in the stool filtrates of the patients with small polyps thus avoiding these false positives for significant pathologic lesions. A disadvantage of this dilution level is that one of the patients with a large polyp and the patient with the villous adenoma also did not have peroxidase activity. This suggests that the optimum dilution level may be less than 10 times.

The data at 1:10/2 filters reveals that 1/76 samples had a small or medium level of peroxidase activity in their filtrate. These results indicate that the test loses its sensitivity at this level of dilution and filtration.

The data considering only medium peroxidase activity as a positive, at a 1:5 dilution of the sample, did reveal the most important concern, the villous adenoma. Only 8 patients tested "positive" using this criteria. The other 68 could have gone home without endoscopy, and no harm would be done.

Only the villous adenoma had to be identified.

The clinical utility of the present invention is that one can use the present invention to define different pathologies in a population by varying the dilution of the sample, the number of filters through which the filtrate is passed and the level of peroxidase activity which constitutes a positive test. For example, if one wishes to detect as many people as possible with fecal occult bleeding, the sample is made less dilute, only 1 layer of filter paper is used, and a small level of peroxidase activity constitutes a positive test. If more specific results are desired, any combination of the dilution of the sample, the number of filters used, or the definition of a positive result can be increased.

This data demonstrates that after acidification and precipitation removal, the presence of peroxidase activity in a stool sample indicates the presence of hemoglobin and serves as a reliable marker of occult gastrointestinal blood and significant pathologic lesion. The above data demonstrate that the present method provides an inexpensive and easy to use FOB test which allows for the differential diagnosis of upper GI bleeding from lower GI bleeding and provide adequate sensitivity, while preventing undesired false positive results.

The foregoing detailed description is given for clearness of understanding only, and no unnecessary limitations should be understood therefrom, as aspects and advantages within the scope of the present invention will be apparent to those skilled in the art.

What is claimed is:

1. A method for detecting the presence of fecal occult blood in fecal samples comprising:

providing a liquid stool sample of fecal material dispersed in solution to thereby dissolve any hematin and hemoglobin present in said fecal material;

preferentially precipitating any hematin present in said liquid stool sample;

separating said hematin precipitate from said liquid stool sample; and subjecting the separated solution comprising said liquid stool sample to a diagnostic assay designed to detect peroxidase activity.

2. The method of claim 1 in which said precipitating step comprises mixing said liquid stool sample with an acidic buffer.

3. The method of claim 2 in which said acidic buffer is a phosphate/citrate buffer.

4. The method of claim 2 in which said liquid stool sample is diluted from about 5 to about 10 times with said acidic buffer.

5. The method of claim 4 in which said liquid stool sample is diluted about 5 times with said acidic buffer.

6. The method of claim 1 in which said hematin precipitate is separated from said liquid stool sample by centrifugation.

7. The method of claim 1 in which said hematin precipitate is separated from said liquid stool sample by filtration.

8. The method of claim 7 in which said hematin precipitate is separated from said liquid stool sample by paper filtration.

9. A method for detecting the presence of fecal occult blood comprising:

mixing a fecal sample with an acidic liquid to form an acidified liquid fecal sample solution;

subjecting said solution to a size-dependent or density dependent separation procedure to separate any precipitate from said solution; and exposing said solution to a diagnostic assay to detect peroxidase activity.

10. The method of claim 9 in which said acidic liquid is an acidic buffer.

11. The method of claim 10 in which said acidic liquid is a phosphate/citrate buffer.

12. The method of claim 11 in which said liquid stool sample is diluted from about 5 to about 10 times with said acidic buffer.

13. The method of claim 12 in which said liquid stool sample is diluted about 5 times with said acidic buffer.

14. The method of claim 9 in which said precipitate is separated from said solution by centrifugation.

15. The method of claim 9 in which said precipitate is separated from said solution by filtration.

16. The method of claim 15 in which said precipitate is separated from said solution by paper filtration.

17. The method of claim 9 further comprising, as prior steps:

administering a laxative purge; and collecting a watery fecal sample to use as said fecal sample.

18. The method of claim 17 in which said acidic liquid is an acidic buffer.

19. The method of claim 18 in which said acidic liquid is a phosphate/citrate buffer.

20. The method of claim 18 in which said liquid stool sample is diluted from about 5 to about 10 times with said acidic buffer.

21. The method of claim 20 in which said liquid stool sample is diluted about 5 times with said acidic buffer.

22. The method of claim 21 in which said precipitate is separated from said solution by centrifugation.

23. The method of claim 17 in which said precipitate is separated from said solution by filtration.

24. The method of claim 23 in which said precipitate is separated from said solution by paper filtration.

25. The method of claim 2 in which said acidic buffer has a pH of from about 3.5 to about 5.

26. The method of claim 10 in which said acidic buffer has a pH of from about 3.5 to about 5.

27. The method of claim 18 in which said acidic buffer has a pH of from about 3.5 to about 5.

* * * * *

UNITED STATES PATENT AND TRADEMARK OFFICE
CERTIFICATE OF CORRECTION

PATENT NO.  : 5,460,969
DATED       : October 24, 1995
INVENTOR    : Fiedler et al.

It is certified that error appears in the above-identified patent and that said Letters Patent is hereby corrected as shown below:

Title page, under Section 19, heading;

"Fielder et al." should be --Fiedler et al.--.

Title page, Section 76;

"Inventors: Paul N. Fielder" should be --Inventors: Paul N. Fiedler--.

Column 5, line 11;

"N" (first occurrence) should be --"M"--.

Signed and Sealed this

Thirty-first Day of December, 1996

Attest:

BRUCE LEHMAN

Attesting Officer

Commissioner of Patents and Trademarks